US006586196B1

(12) United States Patent
Bronstein et al.

(10) Patent No.: US 6,586,196 B1
(45) Date of Patent: Jul. 1, 2003

(54) MULTIPLE ENZYME ASSAYS

(75) Inventors: Irena Bronstein, Newton, MA (US); Christopher Martin, Bedford, MA (US); Corinne Olesen, Bedford, MA (US); John Voyta, Sudbury, MA (US); Yu-xin Yan, Burlington, MA (US)

(73) Assignee: Tropix, Inc., Bedford, MA (US)

( * ) Notice: Subject to any disclaimer, the term of this patent is extended or adjusted under 35 U.S.C. 154(b) by 0 days.

(21) Appl. No.: 09/459,982

(22) Filed: Dec. 14, 1999

Related U.S. Application Data
(60) Provisional application No. 60/112,359, filed on Dec. 15, 1998.

(51) Int. Cl.[7] .......................... C12Q 1/42; C12Q 1/54; C12Q 1/37; C12Q 1/00; G01N 33/53
(52) U.S. Cl. .......................... 435/21; 435/14; 435/23; 435/975; 435/4
(58) Field of Search .......................... 435/21, 14, 23, 435/19, 975, 4

(56) References Cited

U.S. PATENT DOCUMENTS

| | | | |
|---|---|---|---|
| 4,124,388 A | 11/1978 | Bronstein-Bonte et al. | 96/29 |
| 4,322,489 A | 3/1982 | Land et al. | 430/213 |
| 4,340,522 A | 7/1982 | Bronstein-Bonte et al. | 524/766 |
| 4,424,326 A | 1/1984 | Land et al. | 526/265 |
| 4,503,138 A | 3/1985 | Bronstein-Bonte et al. | 430/213 |
| 4,563,411 A | 1/1986 | Bronstein-Bonte et al. | 430/213 |
| 4,931,223 A | * 6/1990 | Bronstein et al. | 435/4 |
| 4,978,614 A | 12/1990 | Bronstein | 435/21 |
| 5,089,630 A | 2/1992 | Bronstein et al. | 549/220 |
| 5,112,960 A | 5/1992 | Bronstein et al. | 536/18.1 |
| 5,145,772 A | 9/1992 | Voyta et al. | 435/4 |
| 5,538,847 A | 7/1996 | Bronstein et al. | 435/6 |
| 5,582,980 A | 12/1996 | Bronstein et al. | 435/6 |
| 5,744,320 A | 4/1998 | Sherf et al. | 435/6 |

OTHER PUBLICATIONS

Alam and Cook, "Reporter Genes: Application to the Study of Mammalian Gene Transcription" Anal. Biochem., 1990; vol. 188:245–254.

Bronstein et al., "Chemiluminescent and Bioluminescent Reporter Gene Assays," Anal. Biochem., 1994; vol. 219:169–181.

Jain et al., "A Chemiluminescent Assay for Quantitation of β–Galactosidase in the Femtogram Range: Application to Quantitation of β–Galactosidase in lacZ–Transfected Cells," Anal. Biochem., 1991; vol. 199:119–124.

(List continued on next page.)

Primary Examiner—Louise N. Leary
(74) Attorney, Agent, or Firm—Steven B. Kelber; Piper Rudnick LLP

(57) ABSTRACT

The present invention discloses multiple enzyme assays which measure the activity of at least one endogenous enzyme in a single aliquot and a method of measuring the activity of multiple enzymes in an aliquot of a cell extract, wherein at least one of the enzymes is an endogenous enzyme. In one embodiment of the invention the activity of a first enzyme is quantified by measuring the light signal produced by degradation of a first enzyme substrate by the first enzyme and the activity of the second enzyme is quantified by measuring the light signal produced by the degradation of a second substrate. In the method of the present invention, both quantifications are performed on the same aliquot of cell extract. Different embodiments of the present invention provide for the detection of more than one endogenous enzyme and for the detection of at least one reporter enzyme and at least one endogenous enzyme. The present invention also discloses kits for detecting the activity of multiple enzymes.

31 Claims, 5 Drawing Sheets

OTHER PUBLICATIONS

Bronstein et al., "Chemiluminescent Reporter Gene Assays for β–Galactosidase, β–Glucuronidase and Secreted Alkaline Phosphatase," Bioluminescence and Chemiluminescence: Fundamental and Applied Aspects (Campbell, et al., eds) Chicester:Wiley, 1997; 20–23.

Martin et al., "Continuous Sensitive Detection of β–Galactosidase with a Novel Chemiluminescent 1,2–Dioxetane," Bioluminescence and Chemiluminescence: Molecular Reporting with Photons (Hastings, et al., eds) Chichester: Wiley, 1997; 525–528.

Bronstein et al., "Chemiluminescence: sensitive detection technology for reporter gene assays," Clin. Chem., 1996; vol. 42, No. 9:1542–1546.

Bronstein et al., "Chemiluminescent Reporter Gene Assays: Sensitive Detection of the GUS and SEAP Gene Products," BioTechniques, 1994; vol. 17:172–177.

Martin et al., "Dual Luminescence–Based Reporter Gene Assay for Luciferase and β–Galactosidase," BioTechniques, 1996; vol. 21, No. 3:520–524.

O'Connor et al., "Quantitation of Two Histochemical Markers in the Same Extract Using Chemiluminescent Substrates," Biotechniques, 1994; vol. 17, No. 3:502–509.

Bronstein et al., "Combined Luminescent Assays for Multiple Enzymes," Bioluminescence and Chemiluminescence. Molecular Reporting with Photons (Hastings, et al., eds) Chichester:Wiley, 1997; 451–457.

* cited by examiner

MULTIPLE ENZYME ASSAYS

This application is a regular National application claiming priority from Provisional Application, U.S. application Ser. No. 60/112,359 filed Dec. 15, 1998. The entirety of that provisional application is incorporated herein by reference.

BACKGROUND OF THE INVENTION

1. Field of the Invention

This invention discloses multiple enzyme assays which measure the activity of at least one endogenous enzyme in a single aliquot of a sample or population of cells and multiple enzymes in a single aliquot of a sample provided that at least one of the enzymes is an endogenous enzyme. The present invention also discloses methods and kits for detecting the activity of multiple enzymes.

2. Background of the Prior Art

A wide variety of reporter gene assays are used in both biomedical and pharmaceutical research for the study of gene regulation and identification of cellular factors and chemical compounds that affect gene expression. Alam and Cook, Anal Biochem, 1990; 188:245–54; Bronstein, et al., Anal Biochem., 1994; 219:169–81. Reporter gene assays are useful in the study of gene regulatory elements because reporter gene activity, i.e., production of the reporter protein, is directly proportional to the transcriptional activity of the regulatory elements of the gene. A reporter gene construct for use in these assays contains one or more gene regulatory elements which are of interest, the minimal sequence requirements for transcription of a functional mRNA, and the coding sequence for a reporter protein. Alam. et al., Anal. Biochem., 188:245–254, 1990. Analysis of constructs containing various deletions within the regulatory region enables mapping of regulatory sequences necessary for transcription and cell specific expression.

Introduction of a reporter gene construct into cells, followed by quantitation of the expressed protein or its activity, provides an indirect measure of gene expression. For example, the sensitive quantitation of reporter gene products is important for analysis of gene expression, signal transduction pathways, identification of protein interactions, and drug discovery. Further, quantitation of the reporter gene enables mapping of the gene promoter and enhancer regions, analysis of gene expression mechanisms, and screening of chemical and natural product libraries for effectors of gene expression.

Chemiluminescent reporter gene assays combine high sensitivity with broad dynamic range, typically 6–7 orders of magnitude. Chemiluminescent 1,2-dioxetane substrates for several reporter enzymes, including β-galactosidase (β-Gal), β-glucuronidase and alkaline phosphatase (AP) are used in highly sensitive assays. These chemiluminescent assays provide superior alternatives to traditional colorimetric, fluorescent, and radioisotopic detection methods. 1,2-dioxetane chemiluminescent substrates have also been used in a dual assay for luciferase and β-galactosidase reporter enzymes. Enzymatic cleavage of each chemiluminescent substrate produces a destabilized dioxetane anion, which fragments and emits light.

Sensitive chemiluminescent assays, not limited to reporter gene assays, have been described using dioxetane substrates. Bronstein, U.S. Pat. No. 4,978,614, incorporated herein by reference. These dioxetane substrates emit visible light following enzyme induced degradation. Enhancement of the chemiluminescent degradation of 1,2-dioxetanes by enhancer substances comprising certain water soluble molecules, such as globular proteins or synthetic polymers that have hydrophobic regions, has been described. Voyta et al., U.S. Pat. No. 5,145,772, incorporated herein by reference. These dioxetane substrates are also used in reporter gene assays for alkaline phosphatase, β-galactosidase, and β-glucuronidase. See e.g., Bronstein. et al., Anal. Biochem., 219:169–181, 1994, and citations therein. The use of dioxetane substrates and enhancers in reporter gene assays has been described in U.S. application Ser. No. 08/579,787, incorporated herein by reference. U.S. application Ser. No. 08/579,787 describes assays in which the products of multiple reporter genes are sequentially quantitated in the same aliquot of cell extract. Simple, rapid, and highly sensitive combined multiple reporter gene assays which detect commonly used reporter genes are described which do not use radioisotopes or require external light sources. These assays produce enhanced levels of light and therefore increase the dynamic range and sensitivity of the assay and enable the use of a wide variety of instruments.

1,2-dioxetane substrates have been incorporated into the GALACTO-LIGHT™, GALACTO-LIGHT PLUS™ and GALACTO-STAR™ assay systems available from Tropix, Inc., for quantitation of β-galactosidase reporter enzyme activity and have been used with mammalian cell cultures, tissue extracts, microinjected frog embryos, protozoan parasites, yeast and bacteria. Jain, et al., Anal Biochem., 1991, 199:119–24; Bronstein, et al. Bioluminescence and Chemiluminescence: Fundamental and Applied Aspects, (Campbell, et al., eds) Chichester:Wiley, 1994, 20–3; Martin, et al., Bioluminescence and Chemiluminescence: Molecular Reporting with Photons, (Hastings, et al., eds.), Chichester:Wiley, 1997, 525–8; Bronstein et al., Clin. Chem., 1996, 42:1542–6. The GUS-LIGHT™ system is used for β-glucuronidase reporter detection. Bronstein. et al., BioTechniques., 1994, 17:172–7. CSPD® substrate is utilized in the PHOSPHA-LIGHT™ assay system for quantitation of either secreted or non-secreted forms of the human placental alkaline phosphatase (PLAP) reporter enzyme. Bronstein, et al., Bioluminescence and Chemiluminescence: Fundamental and Applied Aspects, (Campbell, et al., eds.) Chichester:Wiley, 1994, 20–3; Bronstein, et al., Clin. Chem., 1996, 42:1542–6; Bronstein, et al., BioTechniques, 1994, 17:172–7. The DUAL-LIGHT® system by Tropix, Inc. combines a 1,2-dioxetane with luciferin in a single-tube assay for β-Gal and luciferase reporter enzymes. Martin, et al., BioTechniques, 1996, 21:520–4; Bronstein. et al., Bioluminescence and Chemiluminescence: Molecular Reporting with Photons, (Hastings, et al., eds.) Chichester:Wiley, 1997, 451–7.

Currently, multiple reporter gene assays are commonly used to provide controls for efficiency of transfection. In such assays, cells are transfected with a mixture of two separate plasmids, each having a different reporter gene. The expression of one reporter gene is controlled by different regulatory regions being studied while the other reporter gene, acting as a control, is generally constitutively expressed by a standard promoter or enhancer. The activity of the experimental reporter enzyme is normalized to the activity of the control reporter enzyme.

The measurement of multiple enzyme activities in a single assay provides several capabilities. Transfection normalization can be performed by quantitation of both experimental and control reporter enzymes. Pharmaceutical screening strategies benefit from multiple reporters to distinguish the effect of a compound on a specific transcription factor from a non-specific effect on gene expression, or for multiplex screening of several drug targets. These advantages are described in co-pending U.S. application Ser. No. 08/579,787, filed Dec. 28, 1995.

While reporter enzyme expression is useful for measuring gene regulation, it is also desirable to have a mechanism to measure cell number, cell adhesion, cytotoxicity, and cell proliferation. Reporter enzymes may have limited usefulness for performing these measurements because the promoter used for controlling such a reporter gene preferably acts independent of the exogenous compounds added to the cells for testing gene expression. One skilled in the art would need a gene construct that is expressed at a constant level by the cell regardless of what is added to the test cells. For example, one would have to use a reporter enzyme linked to a strong promoter that is not affected by the test compounds.

The measurement of both a reporter enzyme and endogenous cellular enzyme activity provides assays for normalization of reporter enzyme activity to cellular proteins, or potentially enabling simultaneous quantitation of the reporter activity and cell number, cell proliferation, cell adhesion, or cytotoxicity. It would be desirable to have a method for measuring cell number, cell proliferation, cell adhesion, and cell health that does not require the use of a reporter enzyme to make such measurements.

Techniques for quantitating cell number to normalize or to measure cell proliferation, growth inhibition, cell adhesion or cytotoxic effects are presently known and include various methods for measurement of cellular enzyme activities, vital dye staining, and cellular metabolism. The necessity of testing a separate portion of the sample for measurement of reporter enzyme activity and for measurement of cell number decreases the precision of the assay and may introduce experimental errors into the results. Therefore, a multiple enzyme assay which is sequentially performed on the same aliquot of cell extract would simplify the assay procedure and minimize experimental errors. The use of multiple enzymes can improve the efficiency and information content of high throughput screening for drug discovery. It would be therefore useful to have a method for measuring these factors without requiring the testing of more than one single aliquot of a sample.

U.S. Pat. No. 5,744,320, to Sherf. et al. describes a dual-enzyme reporter system which measures two individual reporter enzymes produced by cells genetically manipulated to simultaneously express two different reporter enzymes. Sherf. et al., describe the use of dual luciferase reporter enzymes and the use of a quench and activate reagent for measuring the activity of those enzymes. However, Sherf et al. fail to describe a method that measures an endogenous enzyme.

Accordingly, it remains a goal to those of ordinary skill in the art to develop a method for measuring multiple enzymes, at least one of which is an endogenous enzyme, e.g., for measuring cell number, cell proliferation, cell adhesion or cytotoxicity in an assay. It is a further goal to those ordinarily skilled in the art to develop a method that measures at least one reporter enzyme and at least one endogenous enzyme in a single aliquot of a sample.

SUMMARY OF THE INVENTION

It is an object of the present invention to provide multiple enzyme assays which measure the activity of at least one endogenous enzyme in a single aliquot, thereby providing internal normalization for a cell number in a single sample.

It is another object of the invention to provide assays to measure the activity of multiple enzymes, wherein the multiple enzymes are at least one enzyme and at least one endogenous enzyme and wherein at least one enzyme is capable of reacting with a dioxetane. The use of 1,2-dioxetane substrates provide sensitive, versatile, and facile chemiluminescent assay systems for quantification of endogenous cellular enzymes.

It is yet another object of the present invention to provide a method of measuring the activity of multiple enzymes, wherein at least one enzyme is an endogenous enzyme, in an aliquot of cells. The method comprises quantifying the activity of a first enzyme by measuring the light signal produced by degradation of a first enzyme substrate by the first enzyme, and then quantifying the activity of a second enzyme by measuring the light signal produced by the degradation of a second substrate by the second enzyme, etc. All quantifications are performed on the same aliquot of cells extract.

The measurement of multiple enzyme activities in a single assay provides advantages. Measurement of both a reporter enzyme and an endogenous cellular enzyme activity is advantageous because it provides assays for normalization of reporter enzyme activity to cellular protein, or potentially enabling simultaneous quantitation of the reporter activity and cell number, cell proliferation, cell adhesion or cytotoxicity.

It is a further object of the present invention to provide kits for detecting the activity of multiple enzymes, at least one of which is an endogenous enzyme, in an aliquot of cells. The kit comprises the reagents for quantifying each of the enzymes, the substrates for each of the enzymes, wherein at least one of the substrates is a dioxetane, and optionally an accelerator solution containing a water soluble polymeric enhancer molecule.

The activity of the multiple enzymes can each be detected sequentially or simultaneously, depending on the instrumentation or detection device used.

DETAILED DESCRIPTION OF THE INVENTION

Figure 1:
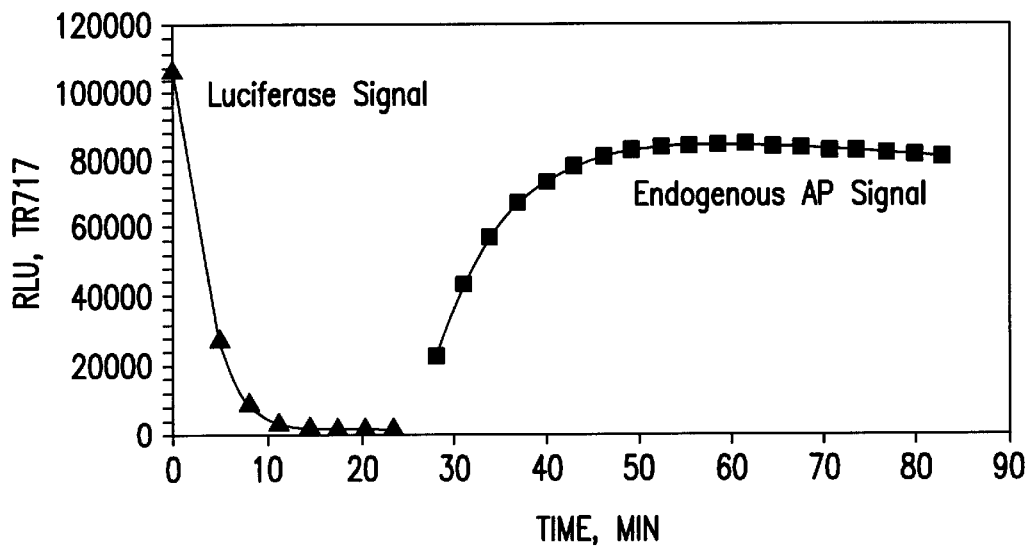
FIG. 1 provides graphical illustration of a dual enzyme assay for luciferase (reporter enzyme) and AP (endogenous enzyme).

The above objects are met by a chemiluminescent assay which relies on the high sensitivity of 1,2-dioxetanes. These dioxetanes, developed by the assignee herein, Tropix, Inc., are the subject of a wide variety of U.S. patents. Generally, dioxetanes are molecules that have a 4-membered ring in which two of the members are adjacent oxygen atoms. Dioxetanes can be thermally, chemically, or photochemically decomposed to form carbonyl products, e.g., esters, ketones, or aldehydes. The decomposition releases energy in the form of light (i.e., luminescence). Specifically, the dioxetane substrates each contain an enzyme-cleavable group that can be cleaved by a corresponding enzyme. When cleaved, a negatively charged group (e.g., an oxygen anion) is left bonded to the dioxetane. This dioxetane anion destabilizes the dioxetane which then decomposes to form a luminescent substance that produces light. The light signal is detected as an indication of the presence and the amount of the enzyme. Thus, by measuring the intensity of the luminescence signal in the presence of excess substrate, the concentration of the corresponding enzyme can be determined.

Highly sensitive chemiluminescent detection of reporter enzymes has been achieved with 1,2-dioxetane substrates in assay formats that are amenable to use in both research-scale and automatable, high throughput pharmaceutical screening platforms. The use of 1,2-dioxetane substrates has been coupled with luciferase reaction reagents for dual detection assays, including multiple reporter enzymes and reporter/endogenous enzyme assays. See, e.g., U.S. application Ser. No. 08/579,787. The previously developed DUAL-LIGHT® assay system is widely used for dual detection of luciferase/β-galactosidase reporter activities.

The present invention relates to multiple enzyme detection assays that enable the detection of multiple enzymes, e.g., both reporter enzyme activity and endogenous enzyme activity, such as luciferase/AP, β-galactosidase/AP, and luciferase/β-galactosidase/AP. These multiple enzyme assays optimize detection sensitivity for both enzyme activities and further simplify assay performance. The activity of the endogenous enzyme is independent of the factor that is manipulated or added to the cells to affect the reporter enzyme activity. Consequently, the activity of the endogenous enzyme provides a marker for cell number which is not linked to the reporter enzyme. This multiple detection capability provides simultaneous measurement of at least one promoter activity with a cell quantitation read-out normalization of cell number, cell growth or proliferation, cell adhesion, or cytotoxicity that is independent of the transcriptional activity of the reporter enzyme. Such a measurement is useful in any type of assay that uses reporter enzymes, from basic laboratory studies of cell function using reporter enzymes to complicated assays used for drug screening.

The assays of the present invention allow the detection of multiple enzymes in a single aliquot of sample (as used herein, sample may include whole cells or cell extracts, the cells can be from mammals, yeast or bacteria). Multiple enzymes can be selected from any combination of reporter and endogenous enzymes, as long as at least one enzyme is an endogenous enzyme. For example, in one embodiment of the present invention, the first enzyme is a reporter enzyme and the second enzyme is an endogenous enzyme. In another embodiment, all of the enzymes are endogenous enzymes. In yet another embodiment, the first and second enzymes are reporter enzymes and the third enzyme is an endogenous enzyme. In a further embodiment, the first enzyme is an endogenous enzyme and the second enzyme is a reporter enzyme. Other combinations apparent to one of ordinary skill in the art can be used in the present assays and methods according to the teachings herein.

Enzymes that are useful in the present invention comprise any protein that is produced from any gene that exhibits enzymatic activity and degrades a substrate to produce a light signal. Examples of such enzymes include luciferase, alkaline phosphatase, β-galactosidase, β-glucuronidase, carboxylesterase, lipases, phospholipases, sulphatases, ureases, peptidases, proteases and others. In preferred embodiments, at least one of the enzymes is a hydrolytic enzyme. In embodiments that use more than one reporter enzyme, it is preferred that the second reporter enzyme is the hydrolytic enzyme. In other embodiments, all of the enzymes are hydrolytic enzymes. Examples of hydrolytic enzymes include alkaline and acid phosphatases, esterases, decarboxylases, phospholipase D, P-xylosidase, β-D-fucosidase, thioglucosidase, β-D-galactosidase, α-D-galactosidase, α-D-glucosidase, β-D-glucosidase, β-D-glucuronidase, α-D-mannosidase, β-D-mannosidase, β-D-fructofuranosidase, β-D-glucosiduronase, and trypsin.

When alkaline phosphatase is used, it is preferable that the substrate comprises a phosphate-containing dioxetane, such as 3-(2'-spiroadamantane)-4-methoxy-4-(3"-phosphoryloxy)phenyl-1,2-dioxetane, disodium salt, or disodium 3-(4-methoxyspiro[1,2-dioxetane-3,2'(5'-chloro)-tricyclo-[3.3.1.1$^{3,7}$]decan]-4-yl)phenyl phosphate, or disodium 2-chloro-5-(4-methoxyspiro{1,2-dioxetane-3,2'-($^{5'}$-chloro)-tricyclo{3.3.1.13,7}decan}-4-yl)-1-phenyl phosphate or disodium 2-chloro-5-($^{4}$-methoxyspiro{1,2-dioxetane-3,2'-tricyclo[3.3.1.13,7]decan}-4-yl)-1-phenzyl phosphate, (AMPPD, CSPD, CDP-Star® and ADP-Star™, respectively).

For assays that use β-galactosidase as an enzyme, the substrate preferably comprises a dioxetane containing galactosidase-cleavable or galactopyranoside groups. The luminescence in the assay results from the enzymatic cleavage of the sugar moiety from the dioxetane substrate. Examples of such substrates include 3-(2'-spiroadamantane)-4-methoxy-4-(3"-β-D-galactopyranosyl)phenyl-1,2-dioxetane(AMPGD), 3-(4-methoxyspiro[1,2-dioxetane-3,2'-(5'-chloro)tricyclo[3.3.1.1$^{3,7}$]-decan]-4-yl-phenyl-β-D-galactopyranoside (Galacton®), 5-chloro-3-(methoxyspiro[1,2-dioxetane-3,2'-(5'-chloro)tricyclo[3.3.1$^{3,}$ $_{7}$]decan-4-yl-phenyl-β-D-galactopyranoside (Galacton-Plus®), and 2-chloro-5-(4-methoxyspiro[1,2-dioxetane-3,2' (5'-chloro)-tricyclo-[3.3.1.1$^{3,7}$]decan]-4-yl)phenyl β-D-galactopyranoside (Galacton-Star®).

In assays that use β-glucuronidase as an enzyme, the substrate comprises a dioxetane containing β-glucuronidase-cleavable groups such as a glucuronide, e.g., sodium 3-(4-methoxyspiro{1,2-dioxetane-3,2'-(5'-chloro)-tricyclo [3.3.1.1$^{3,7}$]decan}-4-yl)phenyl-β-D-glucuronate (Glucuron™). In assays that use carboxyl esterase, the enzyme cleaves the ester group of the dioxetane. In assays that use proteases and phospholipases, the enzymes cleave a suitable enzyme-cleavable group bound to the dioxetane.

In assays that use β-glucosidase as an enzyme, the substrate comprises a dioxetane containing β-glucosidase-cleavable groups such as a glucosidase, e.g., sodium 3-(4-methoxyspiro{1,2-dioxetane-3,2'-(5'-chloro)-tricyclo [3.3.1.1$^{3,7}$]decan}-4-yl)phenyl-β-D-glucuronate (Glucuron™). In assays that use carboxyl esterase, the enzyme cleaves the ester group of the dioxetane. In assays that use proteases and phospholipases, the enzymes cleave a suitable enzyme-cleavable group bound to the dioxetane.

When a reporter enzyme is used, it is preferably selected from the group consisting of luciferase, galactosidase, glucuronidase, alkaline phosphatase, carboxyl esterase, acid phosphatase and glucosidase. In more preferred assays, the reporter enzyme is luciferase, β-galactosidase, or alkaline phosphatase.

Preferably, the endogenous enzyme detected is produced by the cells in an amount that is detectable by the specific chemiluminescent system and instrumentation that is used. One of ordinary skill in the art can readily select an appropriate endogenous enzyme. Examples of useful endogenous enzymes include: alkaline phosphatase, acid phosphatase, glucosidase, glucuronidase, galactosidase, proteases and esterases. Preferred endogenous enzymes are alkaline phosphatase, glucosidase, glucuronidase, and galactosidase. The most preferred endogenous enzyme is glucosidase.

It may be desirable to measure the activity of more than one endogenous enzyme in a single aliquot of cells. The present invention can readily be used to make such measurements. Examples of assays in which all of the enzymes measured are endogenous enzymes include: alkaline phosphatase and esterase; acid phosphatase and alkaline phosphatase; protease and alkaline phosphatase, and phospholipase and alkaline phosphatase.

In the present invention, substrates for enzymes, i.e., the reporter enzymes and endogenous enzymes, comprise any luminescent substrate capable of producing a light signal. Preferably, the substrates for each enzyme are different and at least one substrate is a dioxetane that contains a substituted or unsubstituted adamantyl group, a Y group which may be substituted or unsubstituted and an enzyme cleavable group. Examples of preferred dioxetanes comprise 3-(4-methoxyspiro[1,2-dioxetane-3,2'-(5'-chloro) tricyclo [3.3.1.1$^{3,7}$]-decan]-4-yl-phenyl-β-D-galactopyranoside (Galacton®), 5-chloro-3-(methoxyspiro[1,2-dioxetane-3,2'-(5'chloro)tricyclo[3.3.1$^{3,7}$]decan-4-yl-phenyl-β-D-galactopyranoside (Galacton-Plus®), disodium 6-(4-methoxyspiro-[1,2-dioxetane-3,2'-tricyclo[3.3.1.1$^{3,7}$] decan]-4-yl)-2-phenylbenzothiazolyl-4-phosphate, disodium 2-chloro-5-(4-methoxyspiro{1,2-dioxetane-3,2'-(5'-chloro)-tricyclo{3.3.3.1$^{3,7}$]decan}-4-yl)-1-phenyl phosphate (CDP-Star®), sodium 3-(4-methoxyspiro{1,2-dioxetane-3,2'-(5'-chloro)-tricyclo[3.3.1.1$^{3,7}$]decan}-4-yl) phenyl-β-D-glucuronate (Glucuron™), 3-(4-methoxyspiro{1,2-dioxetane-3,2'-(5'-chloro)-tricyclo [3.3.1.1$^{3,7}$]decan}-4-yl)phenyl-β-D-glucopyranoside (Glucon™), 2-chloro-5-(4-methoxyspiro{1,2-dioxetane-3,2' (5'-chloro)-tricyclo-[3.3.1.1$^{3,7}$]decan)-4-yl)phenyl)-β-D-galactopyranoside, (Galacton-Star), disodium 3-(4-methoxyspiro(1,2-dioxetane-3,2'(5'-chloro)-tricyclo-[3.3.1.1$^{3,7}$]decan)-4-yl)phenyl phosphate (CSPD), disodium 3-chloro-5-(4-methoxyspiro{1,2-dioxetane-3,2'(5'-chloro)-tricyclo-[3.3.1.1$^{3,7}$]decan)-4-yl)-1-phenyl phosphate (CDP), disodium 3-(4-methoxyspiro{1,2-dioxetane-3,2'-tricyclo [3.3.1.1$^{3,7}$]decan}-4-yl)phenyl phosphate (AMPPD), and disodium 2-chloro-5-(4-methoxyspiro{1,2-dioxetane-3,2'-tricyclo[3.3.1.1$^{3,7}$]decan}-4-yl)-1-phenyl phosphate (ADP-Star). These substrates are available from Tropix, Inc., Bedford, Mass.

Preferably, the dioxetane-containing substrate has formula I

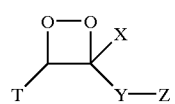

(I)

wherein T is a substituted or unsubstituted cycloalkyl ring having between 6 and 12 carbon atoms, inclusive, in the ring or a polycycloalkyl group having 2 or more fused rings, each ring independently having between 5 and 12 carbon atoms, inclusive, wherein T is bonded to the 4-membered dioxetane ring by a spiro linkage (e.g., a chloroadamantyl or an adamantyl group); Y is a fluorescent chromophore; X is hydrogen, a straight or branched chain alkyl or heteroalkyl group having between 1 and 7 carbon atoms, inclusive, (e.g., methoxy, trifluoromethoxy, hydroxyethyl, trifluoroethoxy or hydroxypropyl), an aryl group having at least 1 ring (e.g., phenyl), a heteroaryl group having at least 1 ring (e.g., pyrrolyl or pyrazolyl), a heteroalkyl group having between 2 and 7 carbon atoms, inclusive, in the ring, (e.g., dioxetane), an aralkyl group having at least 1 ring (e.g., benzyl), an alkaryl group having at least 1 ring (e.g., tolyl), or an enzyme-cleavable group (i.e., a group having a moiety which can be cleaved by an enzyme to yield an electron-rich group bonded to the dioxetane, e.g., phosphate, where a phosphorus-oxygen bond can be cleaved by an enzyme, e.g., acid phosphatase or alkaline phosphatase, to yield a negatively charged oxygen bonded to the dioxetane or OR); and Z is hydrogen, hydroxyl, or an enzyme-cleavable group (as defined above), provided that at least one of X or Z must be an enzyme-cleavable group and that the negatively charged group contains the group Y. The luminescent signal is detected as an indication of the activity of the corresponding enzyme. By measuring the intensity of luminescence, the activity of the corresponding enzyme can be determined.

When X is OR, moiety R is a straight or branched alkyl, aryl, cycloalkyl or arylalkyl of 1–20 carbon atoms. R may include 1 or 2 heteroatoms which may be P, N, S or O. The substituent R is halogenated. The degree of halogenation will vary depending on the selection of substituents on the adamantyl group, on the aryl group, and on the desired enzyme kinetics for the particular application envisioned. Most preferably, R is a trihaloalkyl moiety. Preferred groups include trihalo lower alkyls, including trifluoroethyl, trifluoropropyl, heptafluoro butyrol, hexafluoro-2-propyl, α-trifluoromethyl benzyl, α-trifluoromethyl ethyl, and difluorochloro butyl moieties. The carbon atoms of substituent R may be partially or fully substituted with halogens. When R is aryl, the preferred groups include a phenyl ring substituted with one or more chloro, fluoro, or trifluoromethyl groups, e.g., 2,5-dichlorophenyl, 2,4-difluorophenyl, 2,3,5-trifluorophenyl, 2-chloro-4-fluoro phenyl or 3-trifluoromethyl phenyl. Fluorine and chlorine are particularly preferred substituents, although bromine and iodine may be employed in special circumstances.

Group Y is a fluorescent chromophore or fluorophore bonded to the enzyme-cleavable group Z. Y becomes luminescent upon the dioxetane decomposition caused by the enzyme cleaving of group Z. When Z is cleaved, an electron-rich moiety is formed which destabilizes the dioxetane, leading to its decomposition. This decomposition produces two individual carbonyl compounds, one of which contains group T, and the other of which contains groups X and Y.

The energy released from the decomposition causes compounds containing the X and the Y groups to luminesce (if group X is hydrogen, an aldehyde is produced). Y preferably is phenyl or aryl. The aryl moiety bears group Z, as in formula I, and additionally 1–3 electron active groups, such as chlorine or methoxy, as described in U.S. Pat. No. 5,582,980.

Any chromophore can be used as Y. In general, it is desirable to use a chromophore which maximizes the quantum yield in order to increase sensitivity. Therefore, Y usually contains aromatic groups. Examples of suitable chromophores are further described in U.S. Pat. No. 4,978,614.

Group Z bonded is an enzyme cleavable group. Upon contact with an enzyme, group Z is cleaved, thereby yielding an electron-rich moiety bonded to the chromophore Y. This electron-rich moiety initiates the decomposition of the dioxetane into two individual carbonyl containing compounds, e.g., into a ketone or an ester and an aldehyde if group X is hydrogen. Examples of electron-rich moieties include oxygen, sulfur, and amine or amino anions. The most preferred moiety is an oxygen anion. Examples of suitable Z groups, and the enzymes specific to these groups are given in Table 1 of U.S. Pat. No. 4,978,614 incorporated here by reference. Such enzymes include alkaline and acid phosphatases, esterases, decarboxylases, phospholipase D, β-xylosidase, β-D-fucosidase, thioglucosidase, β-D-galactosidase, α-D-galactosidase, α-D-glucosidase, β-D-glucosidase, β-D-glucuronidase, β-D-mannosidase, β-D-mannosidase, β-D-fructofuranosidase, β-D-glucosiduronase, and trypsin.

The dioxetanes of the present invention may also contain one or more solubilizing substituents attached to any of groups T, Y and X. Solubilizing substituents are substituents which enhance the solubility of the dioxetane in aqueous solution. Examples of solubilizing substituents include carboxylic acids, e.g., acetic acid; sulfonic acids, e.g., methanesulfonic acid; and quaternary amino salts, e.g:, ammonium bromide. The most preferred solubilizing substituent is methane or ethanesulfonic acid.

Other dioxetanes useful in the practice of this invention are described in U.S. Pat. No. 5,089,630; U.S. Pat. No. 5,112,960; U.S. Pat. No. 5,538,847, and U.S. Pat. No. 5,582,980, all of which are incorporated herein by reference and are available from Tropix, Inc., Bedford, Mass.

The order of adding the substrates of the assays of the present invention will vary depending upon the enzymes used. In certain embodiments, the first reporter enzyme substrate and the substrate of the endogenous enzyme are added simultaneously. In other embodiments, the substrate of the endogenous enzyme is added subsequent to the first reporter enzyme substrate.

Preferably, the activity of the first enzyme measured is decreased prior to quantifying the activity of the second enzyme measured. Decreasing the activity of the first enzyme comprises substantially inactivating the first enzyme or decreasing the amount of the first enzyme substrate.

In order to have an accurate assay, the light signal produced by the degradation of the first enzyme substrate must not interfere with the quantification of the light signal produced by the degradation of the second enzyme substrate by the second enzyme. This is accomplished by decreasing the signal produced by the substrate for the first enzyme after measuring the light signal produced by degradation of the first substrate and prior to quantifying the activity of the second enzyme.

In other embodiments, the signal produced from the substrate for the first enzyme is decreased by decreasing the activity of the first enzyme, e.g., by allowing the reaction between the first enzyme and its substrate to proceed until the substrate for the first enzyme is substantially degraded. That is, the light signal produced by degradation of the first substrate is allowed to decay prior to activation or enhancement of the second enzyme, e.g., the endogenous enzyme.

In other embodiments, the signal produced by the substrate for the first enzyme is decreased by decreasing the amount of the first substrate. The appropriate method can be chosen by one skilled in the art based upon the specific enzyme and substrate used. However, in one such embodiment, the substrate concentration is preferably decreased by adding an additional amount of the first enzyme sufficient to degrade the residual first substrate remaining after quantification of the first reporter enzyme. For example, after measuring the light signal produced from the degradation of the first substrate by the first enzyme, e.g., alkaline phosphatase, an amount of alkaline phosphatase is added to the aliquot sufficient to degrade any residual substrate and to prevent any potentially interfering light signal. Since the second substrate is unique to the second enzyme, the presence of the first enzyme in excess will not interfere with the detection of the second light signal. This is useful when dioxetane substrates are used for all the enzymes.

In a different embodiment, decreasing the amount of the first substrate comprises heating the aliquot to degrade the first substrate. Heat inactivation is preferably utilized in embodiments in which the second substrate is added subsequent to inactivation of the first substrate.

In a further preferred embodiment, simultaneous measurement of signals can be effected using appropriate instrumentation, such as the NorthStar™ instrument of the assignee, disclosed in U.S. patent application Ser. No. 60/144,891. The same is incorporated herein by reference.

In one embodiment of the present invention which measures a reporter enzyme, e.g., luciferase, and an endogenous enzyme, e.g., alkaline phosphatase, the luciferase signal is first measured after the addition of the substrate, luciferin (Dual-Light® reagents). Following decay of the luciferase signal, an endogenous enzyme (AP) detection buffer, containing the substrate for AP and an appropriate enhancer (CDP-Star® substrate/Sapphire-II™ enhancer solution) is added and endogenous AP-catalyzed light emission is measured. Maximum light emission from AP reaction is reached within 15 minutes after reagent addition. The results of this assay are shown in FIG. 1. Alternatively, if desired, the AP detection buffer can be added earlier, for example, immediately after the luciferase is measured in order to diminish the luciferase signal (not shown).

Figure 2:
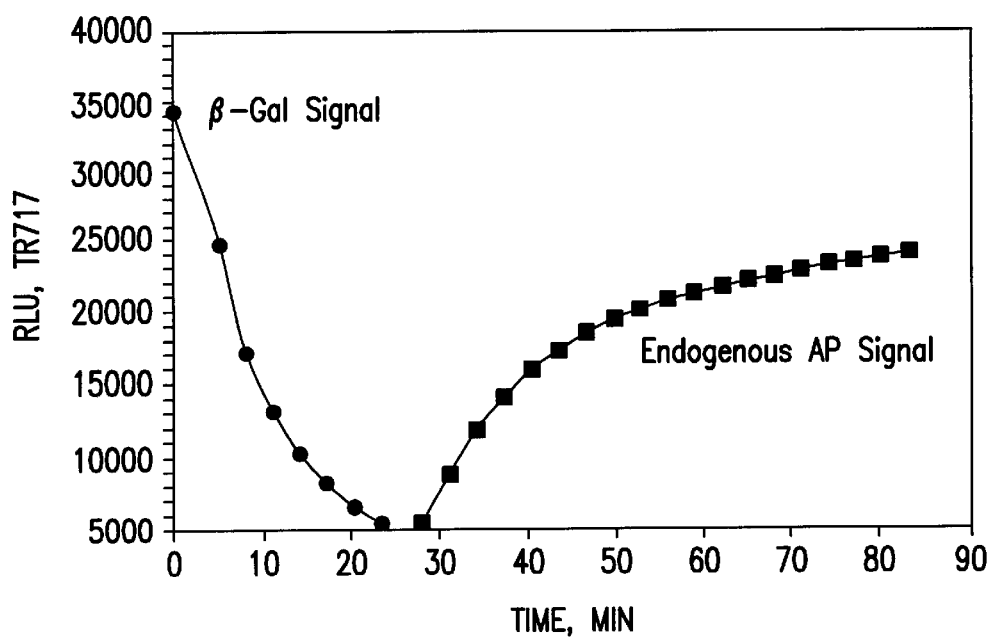
FIG. 2 provides graphical illustration of a dual enzyme assay for β-Gal (reporter enzyme) and AP (endogenous enzyme).

In another preferred embodiment of the present invention which measures a reporter enzyme, e.g., β-galactosidase, and an endogenous enzyme, e.g., alkaline phosphatase, the substrate for the reporter enzyme is added (Galacton® substrate) to each well and incubated for 15 min. An enhancer—(Sapphire-II™) containing accelerator is then injected into each well and the β-galactosidase-catalyzed light emission is measured. Following the decay of the β-galactosidase signal, the substrate for AP (CDP-Star®) is added and the endogenous AP-catalyzed light emission is measured. The results of this assay are shown in FIG. 2.

In certain embodiments of the assay of the present invention which measure the activity of more than one reporter enzyme, e.g., two reporter enzymes and one endogenous enzyme, the first and second reporter substrates are both present in the aliquot during quantification of the activity of the first reporter enzyme. In these embodiments, the presence of the second reporter enzyme, as well as its substrate, does not interfere with the activity of the first reporter enzyme or measurement of the light signal produced by degradation of the first substrate by the first reporter enzyme. In one preferred embodiment, light produced by the degradation of the first substrate occurs at a pH at which the product of the degradation of the second substrate does not produce light. In such an embodiment, the product of the enzymatic reaction with the second substrate does not generate a measurable signal during the first quantification because the environment of the aliquot inhibits light production by the product of this second enzymatic reaction. For example, the measurement of light production by the degradation of the first substrate preferably occurs at a neutral pH. The second reporter enzyme acts on its substrate during the time that the first reporter enzyme acts on its substrate. However, at this pH, no significant production of light from the reaction of the second reporter enzyme and its substrate occurs. It is preferable to allow a predetermined period of time to elapse prior to increasing the pH and measuring light production of the second enzymatic reaction to allow the product of that reaction to accumulate, thereby producing a more intense light signal.

In other embodiments, the presence of the second enzyme does not interfere with the measurement of the light signal from the first enzymatic reaction because the substrate of the second enzyme is absent from the aliquot during this measurement. In such embodiments, the second enzyme is active but there is no substrate on which it can act. In one preferred embodiment, the activity of the second enzyme is induced by the addition of the second substrate after decreasing the activity of the first reporter enzyme or after reduction in the signal produced by the first enzymatic reaction. For example, in an assay using β-galactosidase as the first enzyme and alkaline phosphatase as the second enzyme, light production as a result of the β-galactosidase reaction is optimized at a higher than neutral pH. The increased pH simultaneously activates the second enzyme, alkaline phosphatase, which could produce light which would interfere with the quantification of the activity of the first enzyme. Therefore, in such an assay, it is preferred that the second substrate is added subsequent to the first quantification and most preferably, after that light signal has abated. This addition is readily accomplished and is especially easy when using a detection device as is commonly known in the art.

In preferred embodiments which measure the activity of more than one reporter enzyme and an endogenous enzyme, the substrate for the endogenous enzyme is added subsequent to the decay of light emission from the second reporter enzyme substrate. Preferably, the substrate for the endogenous enzyme initiates light emission. Alternatively, the substrate for the endogenous enzyme is added at a point prior to measurement of the second reporter enzyme and the activity of the endogenous enzyme is increased by methods set forth above, such as altering pH.

In certain preferred embodiments of the present invention, a water soluble polymeric enhancer molecule is added to the light signal produced by enzymatic degradation of the substrate. Preferred polymeric enhancers include bovine serum albumin, human serum albumin, and polymeric quaternary onium salts. Examples of preferred polymeric quaternary onium salts include polyvinylbenzyltrimethyl-ammonium chloride (TMQ), polyvinyl benzyl tributyl ammonium chloride (TBQ) (Sapphire-II™), polyvinylben-zyl benzyldimethylammonium chloride (BDMQ) (Sapphire-I™), polyvinylbenzyltributylphosphonium chloride, and polyvinyl tributyl sulfonium chloride. Other polymeric enhancers include poly(benzyldimethylvinylbenzyl) ammonium chloride and sodium fluoresce in (Emerald™), poly(benzyltributyl)anmuonium chloride and sodium fluorescein (Emerald II™). These enhancers are available from Tropix, Inc., Bedford, Mass.

In other embodiments, an accelerator solution is added prior to quantifying the activity of the second enzyme. Preferred accelerator solutions comprise a water soluble polymeric enhancer molecule at a pH from about 8 to about 14 which is capable of activating the signal production from the degradation of the substrate by the enzyme. In embodiments using just one reporter enzyme and one endogenous enzyme, the accelerator solution activates the signal produced by the degradation of the endogenous substrate by the endogenous enzyme and inactivates the first reporter enzyme. In embodiments which have more than one reporter enzyme, an accelerator solution is added prior to the quantification of the second reporter enzyme, which activates the signal produced by the degradation of the second reporter enzyme substrate and inactivates the first reporter enzyme.

When measuring certain endogenous enzymes it may be necessary to further treat the cells. For example, when measuring endogenous enzymes that are present in the cell or serum in large amounts, the background level may be too high to produce an accurate reading. In such a case, it is preferable to wash the cells prior to the assay. One of ordinary skill in the art can readily determine which endogenous enzymes will require a wash, and will be able to determine the appropriate wash solution, e.g., PBS. For example, in assays that measure AP, the cells are washed once with PBS just prior to the assay.

In certain embodiments of the present invention, the presence of the first substrate enhances the light signal produced by the degradation of the substrate for the second reporter enzyme or the endogenous enzyme. This enhanced signal provides a more sensitive assay. Although the inventors do not intend to be bound by theory, it is believed that the energy produced by the degradation of the second substrate is transferred to the remaining first substrate, thereby enhancing the intensity of the light signal produced. In one preferred embodiment of this method, the first substrate is luciferin. In this embodiment, the substrate for the second enzyme is preferably a dioxetane substrate. It is believed that luciferin is a very efficient energy acceptor and emits a light signal as a result of energy transfer from the excited state generated from the dioxetane decomposition. This produces a greater signal intensity.

Certain preferred embodiments of the present invention further comprise adding a water soluble enhancer molecule which enhances the light signal produced from the enzymatic degradation of the dioxetane substrates by the reporter enzymes or the endogenous enzymes.

Certain water soluble naturally-occurring and synthetic substances, generally macromolecular in nature, enhance the chemiluminescent signal intensity in part by providing a hydrophobic environment. These substances, for example, water soluble globular proteins that contain hydrophobic regions: mammalian serum albumins such as bovine serum albumin (BSA) and human serum albumin (HSA), or water soluble polymeric quaternary onium salts: polyvinylbenzyltrimethyl ammonium chloride (TMQ), polyvinylbenzyltributyl ammonium chloride (TBQ) (Sapphire-II™), polyvinylbenzylbenzyldimethyl ammonium chloride (BDMQ) (Sapphire-I™), and polyvinylbenzyltributyl phosphonium chloride increase the chemiluminescent signal intensity produced by the decomposition of enzymatically cleavable 1,2-dioxetanes in aqueous solutions. Copolymers, such as water soluble quaternary ammonium-phosphonium, ammonium-sulfonium, and sulfonium-phosphonium polymers are useful as enhancer molecules. Other preferred enhancers include poly(benzyldimethylvinylbenzyl) ammonium chloride, sodium fluorescein (Emerald™), poly (benzyltributyl)ammonium chloride, and sodium fluorescein (Emerald II™).

By virtue of the presence of effective amounts of an enhancer substance or substances the intensity of the light emitted in an aqueous medium is increased significantly as compared to the intensity of light emitted in the absence of such enhancers. These compounds enhance the intensity of the chemiluminescent signal from 1,2-dioxetanes by a factor of at least 10%, but usually at least tenfold, and oftentimes by factors of at least 10 to 1,000.

Included among such enhancer substances are macromolecular globular protein, that include hydrophobic regions, generally ones having molecular weights ranging from about 1000 to about 600,000 daltons, as determined by SDS gel electrophoresis. Such substances include mammalian serum albumins such as BSA, HSA and the like; globular proteins such as mammalian IgG, IgE, Protein A, avidins, and the like; and serum lipoproteins, apolipoproteins, and the like.

Synthetic oligomeric or polymeric enhancer substances that can be used in practicing this invention include water soluble polyvinylaryl quaternary onium salts, such as polyvinylbenzyl quaternary ammonium, sulfonium and phosphonium salts having the general formula II:

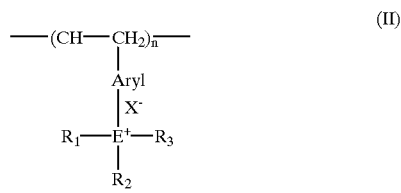

where E+ can be P, N or S.

In this formula each of $R_1$, $R_2$ and $R_3$ can be a straight or branched chain unsubstituted alkyl group having from 1 to 20 carbon atoms, inclusive, e.g., benzyl, methyl, ethyl, n-butyl, t-butyl, cetyl, or the like, a straight or branched chain alkyl group having from 1 to 20 carbon atoms, inclusive, substituted with one or more hydroxzy, alkox-y, e.g., methoxy, ethoxy, benzyloxy or polyoxethyloxy, aryloxy, e.g., phenoxy, amino or substituted amino, e.g., methylamino, amino, e.g., acetamido or cholesteryloxycarbonylamido, or fluoroalkane or fluoroaryl, e.g., heptafluorobutyl groups, an unsubstituted monocycloalkyl group having from 3 to 12 ring carbon atoms, inclusive, e.g., cyclohexyl or cyclooctyl, a substituted monocycloalkyl group having from 3 to 12 ring carbon atoms, inclusive, substituted with one or more alkyl, alkoxy or fused benzo groups, e.g., methoxycyclohexyl or 1,2,3,4-tetrahydronaphthyl, a polycycloalkyl group having 2 or more fused rings, each having from 5 to 12 carbon atoms, inclusive, unsubstituted or substituted with one or more alkyl, alkoxy or aryl groups, e.g., 1-adamantyl or 3-phenyl-1-adamantyl, an aryl, alkaryl or aralkyl group having at least one ring and from 6 to 20 carbon atoms in total, unsubstituted or substituted with one or more alkyl, aryl, or fluoroalkane or fluoroaryl groups, e.g., phenyl, naphthyl, pentafluorophenyl, ethyphenyl, benzyl, hydroxybenzyl, phenylbenzyl or dehydroabietyl; at least two of $R_1$, $R_2$ and $R_3$, together with the quaternary atom to which they are bonded, can form a saturated or unsaturated, unsubstituted or substituted nitrogen-containing, nitrogen and oxygen-containing, or nitrogen and sulfur-containing ring having from 3 to 5 carbon atoms, inclusive, and 1 to 3 heteroatoms, inclusive, and which may be benzoanylated, e.g., 1-pyridyl, 1-(3 alkyl or aralkyl)imidazolium, morpholino, piperidino or acylpiperidino, benzoxazole, benzthiazole or benzamidazole.

The symbol $X^-$ represents a counterion which can include, alone or in combination, moieties such as a halide, i.e., fluoride, chloride, bromide or iodide, sulfate, alkylsulfonate, e.g., methylsulfonate, arylsulfonate, e.g., p-toluenesulfonate, substituted arylsulfonate, e.g., anilinonaphthylenesulfonate (various isomers), lucifer yellow CH and diphenilanthracenesulfonate, perchlorate, alkanoate, e.g., acetate, arylcarboxylate, e.g., fluorescein or fluorescein derivatives, benzoheterocyclicarylcarboxylate, e.g., 7-diethylamino-4-cyanocoumarin-3-carboxylate, or substituted monoaryloxyphosphate, e.g., a 3-(2'-spiroadamantane)-4-methoxy-(3"-phosphoryloxy)phenyl-1,2-dioxetane dianion or other dianions indicated in Formula I, supra.

The symbol n represents a number such that the molecular weight of such polyvinylbenzyl quaternary onium salts will range from about 800 to about 200,000, and preferably from about 20,000 to about 70,000, as determined by intrinsic viscosity or LALLS techniques.

Illustrative of such water soluble poly(vinylbenzyl quaternary ammonium salts) are TMQ, BDMQ, and the like.

Water soluble acetals of a polyvinylalcohol and a formylbenzyl quaternary onium salt, having the formula III:

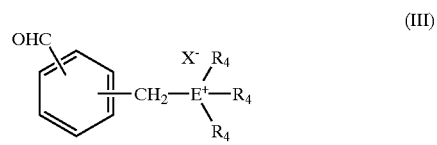

wherein E+ can be P, N or S and each $R_4$ is the same or a different aliphatic substituent and $X^-$ is an anion, as disclosed and claimed in Bronstein-Bonte et al., U.S. Pat. No. 4,124,388. The individual vinylbenzyl quaternary onium salt monomers used to prepare the polyvinylbenzyl quaternary onium salts of formula II above can also be copolymerized with other vinylbenzyl quaternary onium salt monomers whose polymers are depicted in formula III, or with other ethylenicaly unsaturated monomers having no quaternary onium functionality, to give polymers such as those disclosed and claimed in Land et al., U.S. Pat. No. 4,322,489; Bronstein-Bonte et al., U.S. Pat. No. 4,340,522; Land et al., U.S. Pat. No. 4,424,326; Bronstein-Bonte et al., U.S. Pat. No. 4,503,138 and Bronstein-Bonte, U.S. Pat. No. 4,563,411. All of these polymers can also be used as enhancer substances in practicing this invention. Preferably these quaternized polymers will have molecular weights within the ranges given above for the polyvinylbenzyl quaternary ammonium salts of formula III.

Other water soluble oligomeric, homopolymeric, and copolymeric materials can be used as enhancer substances in addition to or instead of the foregoing polymers and are further described in U.S. Pat. No. 5,145,772, and are available from Tropix, Inc., Bedford, Mass.

The amount of enhancer substance used varies depending on the particular enhancer chosen and the amount and type of chemiluminescent compounds present. The necessary amount can be readily determined by one ordinarily skilled in the art based upon the present teachings. Furthermore, the disclosure contained within U.S. Pat. No. 5,145,772 would assist one skilled in the art in practicing this invention.

The enhancer molecule can be added at any point in the present invention. If the first substrate, but not the second substrate, is a dioxetane, the enhancer is preferably added prior to or simultaneous to the quantification of the first enzyme. If the second substrate, but not the first substrate, is a dioxetane, the enhancer can be added at any time, but is preferably added subsequent to the quantification of the first enzyme and prior to or simultaneous to the quantification of the second enzyme. If both the first and second substrates are dioxetanes, the enhancer molecule is preferably added prior to any quantification or simultaneous to the first quantification. In this last embodiment, one enhancer can be used to enhance the light signals produced by the decomposition of both enzyme substrates. Alternatively, a different enhancer is used for each enzyme substrate.

In some embodiments of the present invention, there is an incubation period subsequent to the quantification of the light signal produced by the substrate for the first enzyme, in part, to allow the light signal produced by the first substrate to diminish. The length of the incubation period will vary depending on the concentration of the first reporter enzyme and the half-life of the light signal produced by the substrate. If the first enzyme is present in high concentrations, it may interfere with the quantification of low levels of the subsequent enzymes. A longer incubation period will decrease the residual light signal from the substrate for the first reporter enzyme. Taking into account the teachings of the present invention, the appropriate length of the incubation period can readily be determined by one ordinarily skilled in the art.

The methods according to the present invention provide a rapid, highly sensitive, non-isotopic method for sequentially detecting multiple enzyme activities in a single aliquot of cells. Specifically, the present invention also relates to a method of measuring the activity of multiple enzymes, at least one of which is an endogenous enzyme, in a single aliquot of cells. The method comprises quantifying the activity of a first enzyme by measuring the light signal produced by degradation of a first enzyme substrate by the first enzyme, and then quantifying the activity of the second enzyme by measuring the light signal produced by the degradation of a second substrate by the endogenous enzyme, wherein both quantifications are performed on the same aliquot of cell extract. The intensity of the luminescent signal produced from the substrates is a function of the activity of the enzyme, i.e., the effectiveness of the enzyme in terms of its ability to degrade its substrate and/or the amount of enzyme present.

In a preferred embodiment, the method of measuring the activity of multiple enzymes in an aliquot of a cells extract wherein the enzymes are at least one reporter gene product and at least one endogenous enzyme comprises adding a first substrate, which is the substrate of a first reporter enzyme, and a second substrate, which is the substrate of the endogenous enzyme, to an aliquot of the cell extract. In this preferred embodiment, the first substrate is luciferin, the second substrate comprises a dioxetane, and the endogenous enzyme is a hydrolytic enzyme. First, the activity of the first reporter enzyme is measured. Then, an accelerator solution containing an enhancer molecule is added. The accelerator solution substantially inactivates the first reporter enzyme and simultaneously increases the chemiluminescent signal of the substrate of the endogenous enzyme. Next, the substrate for the endogenous enzyme is added and the activity of the endogenous enzyme is measured. Preferably, the first reporter enzyme is luciferase and the endogenous enzyme is selected from the group consisting of alkaline phosphatase, acid phosphatase, galactosidase, glucosidase, glucuronidase, protease and esterases. A more preferred endogenous enzyme is glucosidase.

The methods of the present invention are particularly useful in measuring the transcriptional activity of cells transfected with at least one reporter gene and allowing the measurement of cell number, cell proliferation, cell adhesion or cytotoxicity by measuring at least one enzyme endogenous to the cell.

Transfection of cells is accomplished by methods known in the art. See e.g., Alam, J. and Cook, J. K., Anal. Bioch. 188: 245–254 (1990). In embodiments of the present invention that measure at least three enzymes, i.e., at least two reporter enzymes and an endogenous enzyme, cells are co-transfected with a DNA mixture of two separate plasmids, each having a different reporter gene. One plasmid has a reporter gene which is regulated by a known control promoter. This reporter gene acts as a control. The second plasmid has a second reporter gene which is controlled by the regulatory region being studied. Transcription of each reporter gene is analyzed by measuring the activity of its product, i.e., a "reporter enzyme". The activity of the second reporter enzyme is typically normalized to the activity of the first reporter enzyme. Id. at 249.

In certain methods of the present invention the activity of the second enzyme is modulated prior to measuring the light signal produced by the degradation of its substrate. The activity of the second enzyme is modulated by adding the substrate for the endogenous enzyme or activating the endogenous enzyme. In certain embodiments, the activity of the second enzyme is modulated by increasing the pH of the aliquot, as discussed above.

In certain preferred embodiments, the method of measuring the activity of multiple enzymes further comprises adding an enzyme detection buffer subsequent to the quantification of the first reporter enzyme. Preferably the enzyme detection buffer comprises the substrate for the second enzyme and an enhancer. The enzyme detection buffer may also contain an accelerator solution, i.e., an enhancer in a high pH buffer, as described further below.

In addition, the present invention provides a method of measuring the activity of multiple enzymes, wherein the enzymes comprise more than two reporter gene products and an endogenous enzyme in the same aliquot of cell extract. A number of factors determine the volume of the aliquot of cell extract used, such as, the availability of the sample, instrumentation, and availability of reagent. Preferably, the volume of the aliquot of cell extract will be determined on the basis of size of the apparatus or plate used to hold extract, the apparatus for determining the signal, environmental conditions, and other parameters familiar to those of ordinary skill in the art.

The methods of the present invention may be performed in any luminometer, but preferably in luminometers that have automatic injectors, or other instrumentation which enables the measurement of light emission. The method can also be performed in a luminometer equipped with a single injector. The method can be performed using manual injection if the light signal of each sample is measured after approximately the same time interval subsequent to the addition of the reagent to the samples. As aforesaid, the activity of the enzymes can be detected sequentially, or simultaneously, depending on the instrumentation used.

In one preferred embodiment, the method comprises first quantifying the activity of a first reporter enzyme in an aliquot of the cell extract by measuring the light signal produced by degradation of a first substrate and then decreasing the activity of the first reporter enzyme. Next, the activity of a second reporter enzyme in the aliquot of the cell extract is quantified by measuring the light signal produced by degradation of a second substrate. Preferably, the second enzyme is a hydrolytic enzyme capable of reacting with a dioxetane. The second enzyme can be any enzyme, but is preferably selected from the following enzymes: β-galactosidase, β-glucuronidase, alkaline phosphatase, and carboxyl esterase. The most preferable embodiment is where the second enzyme comprises β-galactosidase. The activity of an endogenous enzyme in the same aliquot of the cell extract is then quantified by measuring the light signal produced by degradation of the substrate for the endogenous enzyme. All quantifications are sequentially performed on the same aliquot of cell extract.

In another embodiment, the first and second reporter substrates and endogenous enzyme substrate are different and at least one of the substrates is a dioxetane. The present invention includes methods that further comprise inducing the signal produced by the degradation of the second reporter substrate by the second reporter enzyme and then inducing the activity of the endogenous enzyme.

In one embodiment of the method that measures the activity of two reporter enzymes and one endogenous enzyme, the substrate for a first reporter enzyme and a second substrate which is the substrate for a second reporter enzyme are added to an aliquot of the cell extract. In a preferred embodiment, the first enzyme is a luciferase, the second enzyme is a hydrolytic enzyme, the first substrate is luciferin, and the second substrate is a dioxetane. The reporter enzyme is preferably selected from β-galactdsidase, β-glucuronidase, alkaline phosphatase, carboxyl esterase, and luciferase. A more preferred reporter enzyme is luciferase.

In this preferred embodiment, the substrate for the first enzyme is added at the same time as the substrate for the second enzyme and the chemiluminescent signal produced by the substrate for the first reporter enzyme is measured by measuring the light signal produced from luciferase-luciferin reaction while simultaneously adding the substrate for the second enzyme. An accelerator solution which substantially inactivates the first reporter enzyme by increasing the pH of the aliquot is then added. Then the increased pH of the aliquot activates the light production from the accumulated product of the second reporter enzyme-second substrate reaction. The accelerator solution includes an enhancer, such as polyvinylbenzyltributyl ammonium chloride, which, as stated above, enhances the light signal produced by the decomposition of the dioxetane substrate for the second reporter enzyme. The activity of the second reporter enzyme is then measured by reading the chemiluminescent signal intensity in the same aliquot of the cell extract. In embodiments where luciferin is used as the first substrate, the presence of this substrate further enhances the light signal produced by the second substrate. In preferred embodiments, following the decay of light emission from the second reporter enzyme, a 1,2-dioxetane substrate is added to initiate light emission from the endogenous enzyme, e.g., alkaline phosphatase. In this example, the substrate is CDP-Star® 1,2-dioxetane. This sequential detection protocol enables the detection of three enzyme activities, including two reporter enzymes and one endogenous enzyme, in a single tube/well assay of a single sample of cell extract.

Figure 3:
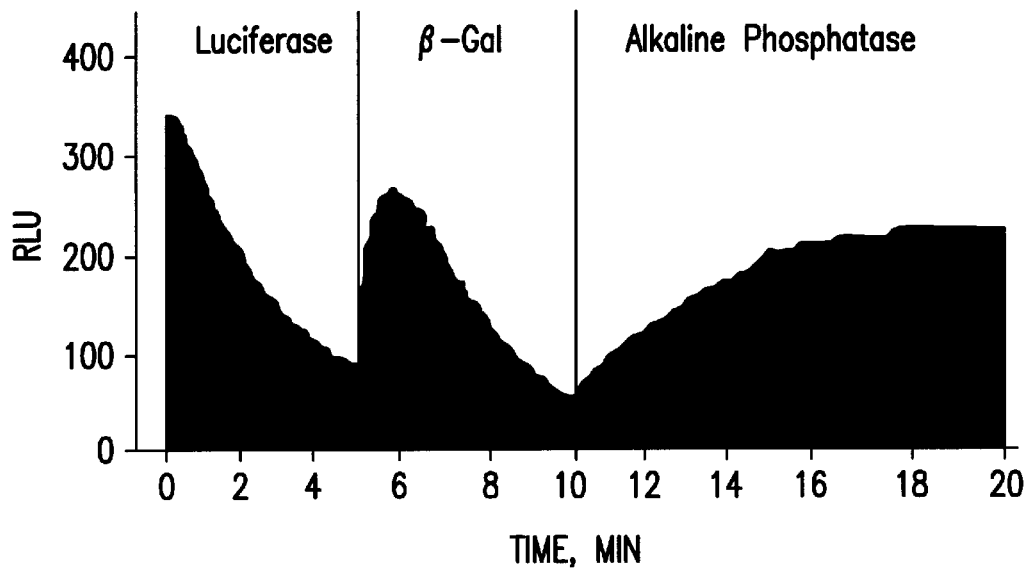
FIG. 3 provides graphical illustration of a multiple enzyme assay for luciferase (reporter enzyme), β-galactosidase (reporter) and alkaline phosphatase (endogenous enzyme).

FIG. 3 demonstrates the sequential detection of luciferase, β-galactosidase, and alkaline phosphatase activities, with luciferin, Galacton®, and CDP-Star®, respectively. The assay was performed with a mixture of Ψ2BAGα and NIH/3T3 cell extracts, which contains β-galactosidase reporter enzyme and endogenous alkaline phosphatase activity, with added purified luciferase, as described below in Example 3. The extract mixture and amount of luciferase added were adjusted to generate similar light intensities for each enzyme. Luciferase-catalyzed light emission is measured first, following the addition of both luciferin substrate and substrate. β-galactosidase-catalyzed cleavage of Galacton® substrate proceeds during the decay of the luciferase signal, and light emission from the breakdown of the Galacton® anion intermediate is triggered by the addition of an accelerator, a high pH solution containing enhancer. Following sufficient decay of the β-galactosidase signal, CDP-Star® is added, which initiates a glow light emission reaction catalyzed by alkaline phosphatase. Detection of luciferase followed immediately by endogenous alkaline phosphatase was also performed (FIG. 1).

In embodiments of the present invention using more than one reporter enzyme, e.g., two reporter enzymes, the presence of the second reporter enzyme in the aliquot must not interfere with the activity of the first reporter enzyme or measurement of the light signal produced by that first enzyme. In these embodiments, the method further comprises increasing the enzymatic activity of the second reporter enzyme subsequent to quantifying the activity of the first enzyme. This can be accomplished by methods known in the art to activate enzyme activity. In especially preferred embodiments, the pH of the aliquot is adjusted to create an environment in which the second enzyme is active prior to the second quantification. For example, in some embodiments, using alkaline phosphatase as the second reporter enzyme, the pH of the aliquot is raised because the activity of alkaline phosphatase is increased at alkaline pH.

In some preferred embodiments, the signal produced from the substrate for the first enzyme is decreased by substantially inactivating the first reporter enzyme. Methods of substantially inactivating the first enzyme are known in the art. However, these methods must not interfere with the measurement of the activity of the second enzyme. For example, in one embodiment, the first enzyme is substantially inactivated by altering the pH of the aliquot. The pH can be altered by adding acids or bases to the aliquot, depending on the enzyme, to provide an environment which is inhospitable to the first enzyme. Preferably the pH of the aliquot is increased. This increased pH inactivates the first enzyme, thereby preventing it from further degrading its substrate and producing a light signal. In another embodiment, the aliquot is heated to degrade the first enzyme. Alternatively, specific inhibitors can be added to inactivate the first enzyme. Examples of inhibitors include alcohols such as isopropanol or ethanol, surfactants such as cetyl trimethyl ammonium bromide (CTAB) or substrate analogs which bind to, and inactivate the enzyme.

As described above, the methods of the present invention measure the activity of an endogenous enzyme. They enable the normalization of cells in an assay by providing a measurement of cell number independent of the activity of reporter enzyme or enzymes present in the sample. The present methods also enable the monitoring of cell proliferation, which may be affected by the test conditions, also independent of the activity of reporter enzymes. For example, when certain compounds are added to the cells that produce a non-specific effect, e.g., growth factor, are added to the cells, it is desirable to confirm that regular cell functions are occurring, as opposed to those that are controlling the reporter construct. The methods of the present invention enable that confirmation.

Finally, the cytotoxic effects of test conditions, i.e., potential drugs, changes in temperature or pH, etc. can be evaluated by the present methods. One measure of cytotoxicity can be obtained by measuring the amount or changes in activity of endogenous enzymes that are released from the cells into the culture medium. In addition, cytotoxicity can potentially be determined by measuring enzyme activity within cells as an indicator of viable cells present. This provides a measure of cell lysis, which is one measurement of cytotoxicity. Such an assay can be performed using the methods of the present invention with the cells present in the medium.

The present invention also provides kits for detecting the activity of multiple enzymes in a single aliquot of a cell extract, provided that at least one of the enzymes is an endogenous enzyme. Such a kit comprises the reagents for quantifying each of the enzymes and the substrates for each of the enzymes, wherein at least one of the substrates is a dioxetane. The kit can also comprise an accelerator solution containing a water soluble polymeric enhancer molecule. Optionally, the accelerator solution comprises a water soluble polymeric enhancer molecule at a pH from about 8 to about 14, to raise the pH, to decrease the activity of the first enzyme, and to increase the signal produced from the enzymatic degradation of the second substrate by the second enzyme (e.g., in a three enzyme assay), or to decrease the activity of a first reporter enzyme and increase the signal produced by degradation of the substrate of the endogenous enzyme (e.g., in a reporter/endogenous enzyme assay).

The polymeric enhancer preferably comprises bovine serum albumin, human serum albumin or polymeric quaternary onium salts. The polymeric quaternary onium salts comprise polyvinylbenzyltrimethyl-ammonium chloride (TMQ), polyvinylbenzyltributylammonium chloride (TBQ) (Sapphire-II™), polyvinylbenzyl benzyldimethylammonium chloride (BDMQ) (Sapphire™), or polyvinylbenzyl-tributyl phosphonium chloride, poly(benzyldimethylvinylbenzyl)ammonium chloride and sodium fluorescein (Emerald™), and poly(benzyltributyl) ammonium chloride and sodium fluorescein (Emerald II™). Preferred polymeric enhancers include polyvinylbenzyltrimethyl-ammonium chloride (TMQ), polyvinylbenzyltributylammonium chloride (TBQ) (Sapphire-II™), polyvinylbenzyl benzyldimethylammonium chloride (BDMQ) (Sapphire™), or polyvinylbenzyl-tributyl phosphonium chloride.

The following examples are provided to illustrate the present invention and are not intended in any way to limit the scope of the invention.

EXAMPLES

Reagents, Cell Lines and Instrumentation

Assay reagents, including Lysis Solution, CDP-Star®, Galacton® and Sapphire-II™ and polymeric enhancer, Phospha-Light™ Assay Buffer, Dual Light Buffer A and B, and plasmid pCMV/β-Gal, are available from Tropix, Inc., Bedford, Mass.

Cell lines include Ψ2BAGα (CRL-9560, ATCC, Rockville, Md.), an NIH/3T3 derivative that constitutively expresses bacterial β-galactosidase from a stably inserted retroviral construct, cultured in DMEM/10% calf serum; and AP3T3b (O'Connor, K. L. et al., Biotechriques, 1994; 17: 502–9); NIH/3T3 (CRL-1658, ATCC) mouse embryonic fibroblasts, cultured in DMEM/10% calf serum; a stably transfected Balbc/3T3 derivative that constitutively expresses non-secreted placental alkaline phosphatase, cultured in DMEM/10% calf serum. All culture media and serum was obtained from Sigma (St. Louis, Mo). Plasmid pGL3, constitutively expresses luciferase reporter from an SV40 promoter/enhancer. SuperFect™ transfection reagent was obtained from QIAGEN (Valencia, Calif.). Transfections were performed according to the supplied protocol.

Assays were performed in tissue culture-treated, clear-bottomed, opaque white 96-well microplates (Cat. 3610, Corning Costar Corps, Action, Mass.). Light emission was measured with either the TR717™ microplate luminometer (Tropix) or the Turner Model 20e single tube luminometer (Turner Designs, Mountain View, Calif.).

Example 1

Luciferase (Reporter)/AP (Endogenous) Assay Protocol pGL3-transfected NIH/3T3 cells were seeded in 96-well microplates and washed once with PBS prior to assay. First, the luciferase signal was measured using Dual-Light® reagents. 25 μl of Dual-Light® Buffer A containing 0.1% Triton X-100 was then added to each well, and 75 μl/well of Dual-Light® Buffer B was injected. Light emission was then measured with a TR717 luminometer. Following the decay of the luciferase signal, 100 μl of a CDP-Star® substrate/Sapphire-II™ enhancer solution was added and endogenous AP-catalyzed light emission was measured. Maximum light emission from the AP reaction was reached within 15 minutes of the reagent addition. The results of the assay are shown in FIG. 1. It was noted that upon an earlier addition of AP detection buffer, (e.g., immediately after luciferase was measured), the luciferase signal was diminished (this effect not shown).

Example 2

β-Galactosidase (Reporter)/AP (Endogenous) Assay Protocol pCMV/β-Gal-transfected NIH/3T3 cells were seeded in $2 \times 10^4$ cells/well in 96-well microplates and washed once with PBS prior to assay. Next, 100 μl of a reaction buffer containing HEPES, $MgCl_2$, Triton X-100, and/Galacton® substrate was added to each well and incubated for 15 min. 50 μl of a Sapphire-II™ enhancer-containing accelerator was then injected into each well and the β-galactosidase-catalyzed light emission was measured with a TR717 luminometer. Following the decay of the β-galactosidase signal, 50 μl of diluted CDP-Star® substrate was added and the endogenous AP-catalyzed light emission was measured. The results of the assay are shown in FIG. 2.

Example 3

Triple enzyme Assay: Luciferase (Reporter)/β-Galactosidase (Reporter)/AP (Endogenous) Assay Protocol 25 μl of Dual-Light® Buffer A was added to 10 μl of lysate and incubated for 30 sec. Next, 100 μl of Dual-Light® Buffer B containing 1:100 Galacton® was added. After 4.5 min., 100 μl of Buffer C containing 0.3 mol/L diethanolamine/20% enhancer was added. Finally, at 10 min., 100 μl of 1.2 mmol/L CDP-Star® in Buffer C was added. Light emission was continuously measured throughout the assay with a Turner Model 20e luminometer.

The extract was assayed sequentially for luciferase reporter, β-Gal reporter, and finally for endogenous alkaline phosphatase enzyme activities. Luciferase and β-Gal activities were measured with modified Dual-Light® assay reagents using the Galacton® 1,2-dioxetane substrate for β-Gal with a modified accelerator formulation. The addition of an enhancer-containing accelerator initiated light emission from the β-Gal-catalyzed decomposition reaction with Galacton® substrate and quenched the luciferase-catalyzed light emission. Following the decay of light emission from the Galacton® substrate, the CDP-Star® 1,2-dioxetane substrate was added to initiate light emission from the alkaline phosphatase. This sequential detection protocol enables the detection of three enzyme activities, including two reporter enzymes and one endogenous enzyme, in a single tube/well assay of a single sample of cell extract.

Example 4

Kinetics of Luciferase (Reporter)/β-Glucosidase (Endogenous) Assay

Figure 4:
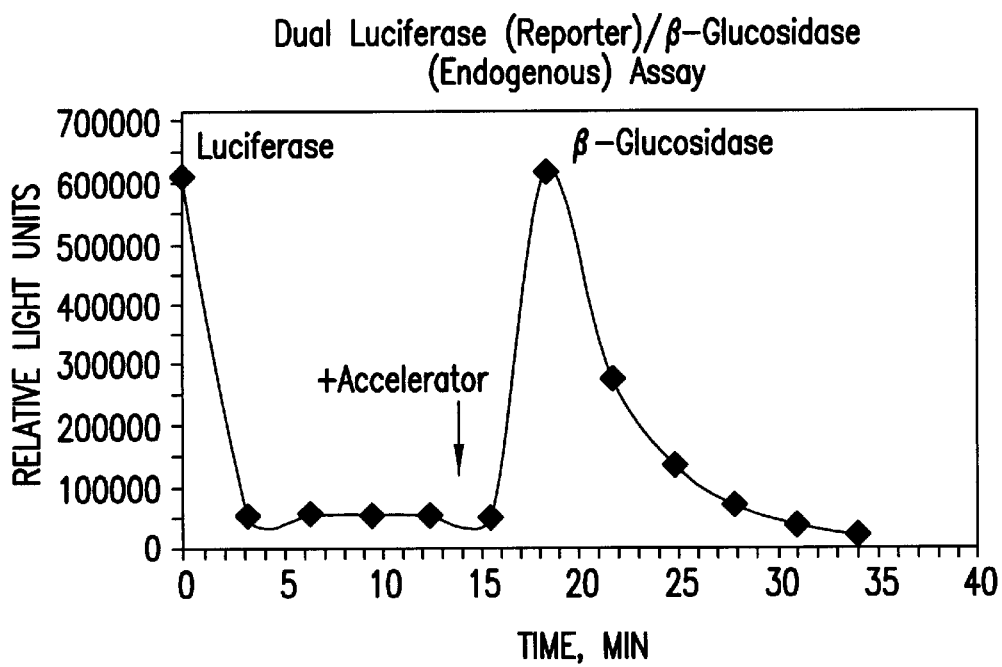
FIG. 4 provides graphical illustration of the kinetics of a dual enzyme assay for luciferase (reporter enzyme) and β-glucosidase (endogenous enzyme).

NIH/3T3 mouse embryonic fibroblasts transfected with pGL3-Control, which constitutively expresses luciferase reporter enzyme from an SV40 promoter/enhancer, were seeded into clear-bottom/white-side tissue culture-treated 96-well microplates in DMEM/10% CS ($5 \times 10^4$ cells/well). Prior to the assay, the culture medium was removed from the wells and the cells were washed once with 200 µl of PBS. All assay incubations were performed at room temperature. A modified luciferase reaction buffer, containing Triton X-100 and Glucon™ substrate was added (25 µl/well) and the plates were incubated for 15 min. It is noted that during this incubation, the β-glucosidase-catalyzed deglycosylation of Glucon™ produces an intermediate that accumulates. At this pH, there is no appreciable β-glucosidase activity. Next, the plates were placed in a TR717 microplate luminometer and 75 µl/well of buffer containing luciferin was injected. Luciferase-catalyzed light emission was measured for 1 sec. immediately after injection. The luciferase signal occurred as a "flash", and decayed rapidly. After approximately 15 min., an accelerator solution containing Sapphire-II™ enhancer was injected (100 µl/well) and light emission was repeatedly measured (1 sec/well). The high pH accelerator solution triggered light emission from the decomposition of the accumulated Glucon™ reaction product. The results of the assay are shown in FIG. 4. It was noted that the addition of an accelerator caused quenching of any residual luciferase signal (not shown), and thus it is not necessary to wait for the luciferase signal to completely decay.

Example 5

Detection range of Luciferase (Reporter)/β-Glucosidase (Endogenous) Assay

Figure 5:
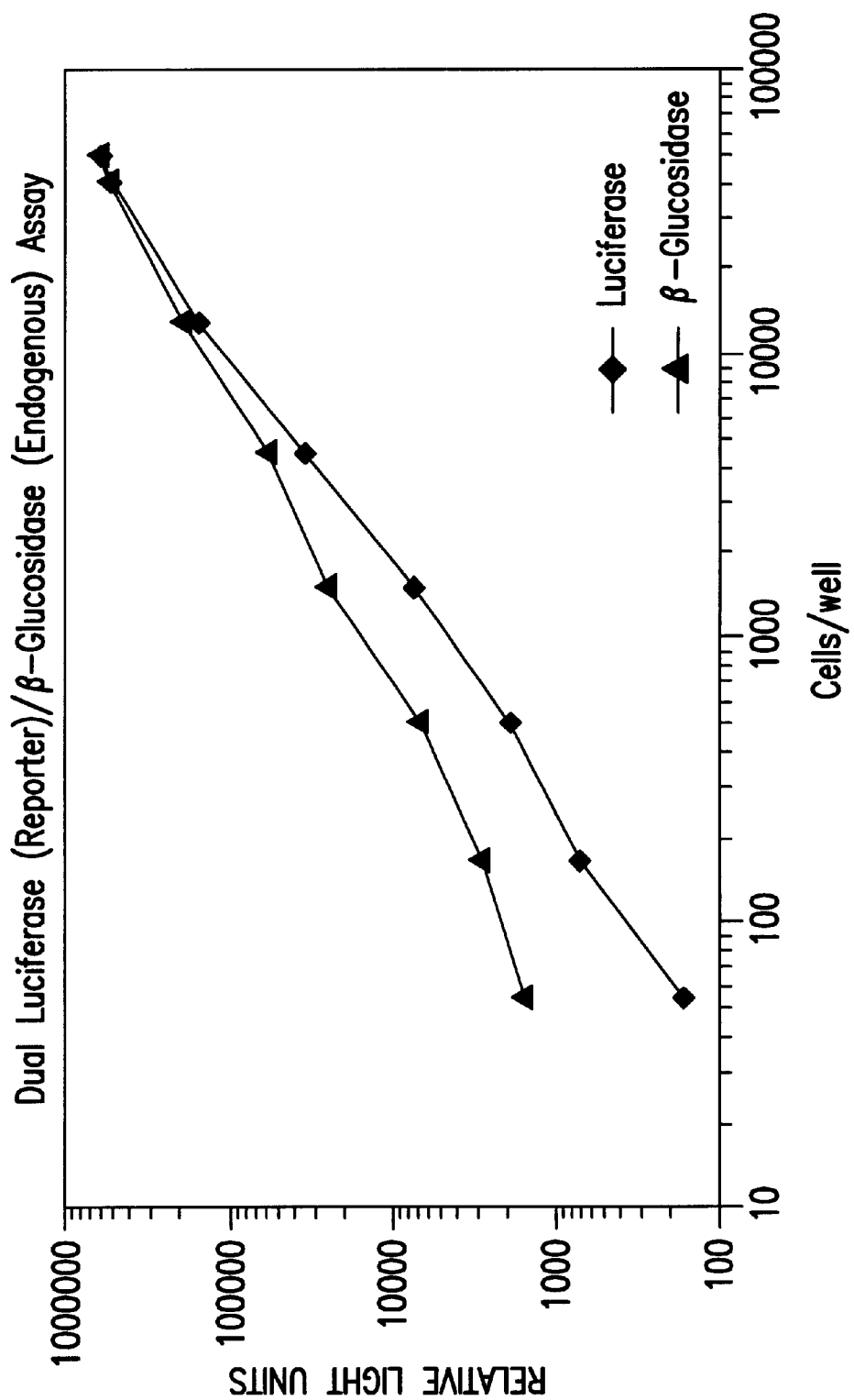
FIG. 5 provides graphical illustration of the detection range of a dual enzyme assay for luciferase (reporter enzyme) and β-glucosidase (endogenous enzyme).

NIH/3T3 mouse embryonic fibroblasts transfected with pGL3-Control, which constitutively expresses luciferase reporter enzyme from an SV40 promoter/enhancer, were seeded into clear-bottom/white-side tissue culture-treated 96-well microplates in DMEM/10% CS. Prior to the assay, the culture medium was removed from the wells and the cells were washed once with 200 µl of PBS. All assay incubations were performed at room temperature. A modified luciferase reaction buffer containing Triton X-100 and Glucon™ substrate was added (25 µl/well) and the plates were incubated for 15 min. Next, the plates were placed in a TR717 microplate luminometer and 75 µl/well of buffer containing luciferin was injected. Light emission was measured for 1 sec. immediately after injection. After approximately 15 min., an accelerator solution containing SapphireII™ enhancer was injected (100 VI/well) and light emission was measured repeatedly (1 sec/well). Quantitation of both luciferase reporter enzyme and endogenous β-glucosidase activity was achieved with a dynamic range spanning three orders of magnitude of cell number, from less than 100 to 50,000 transfected cells. The results of this assay are shown in FIG. 5.

Example 6

Kinetics of PLAP (Reporter)/β-Glucosidase (Endogenous) Assay

Figure 6:
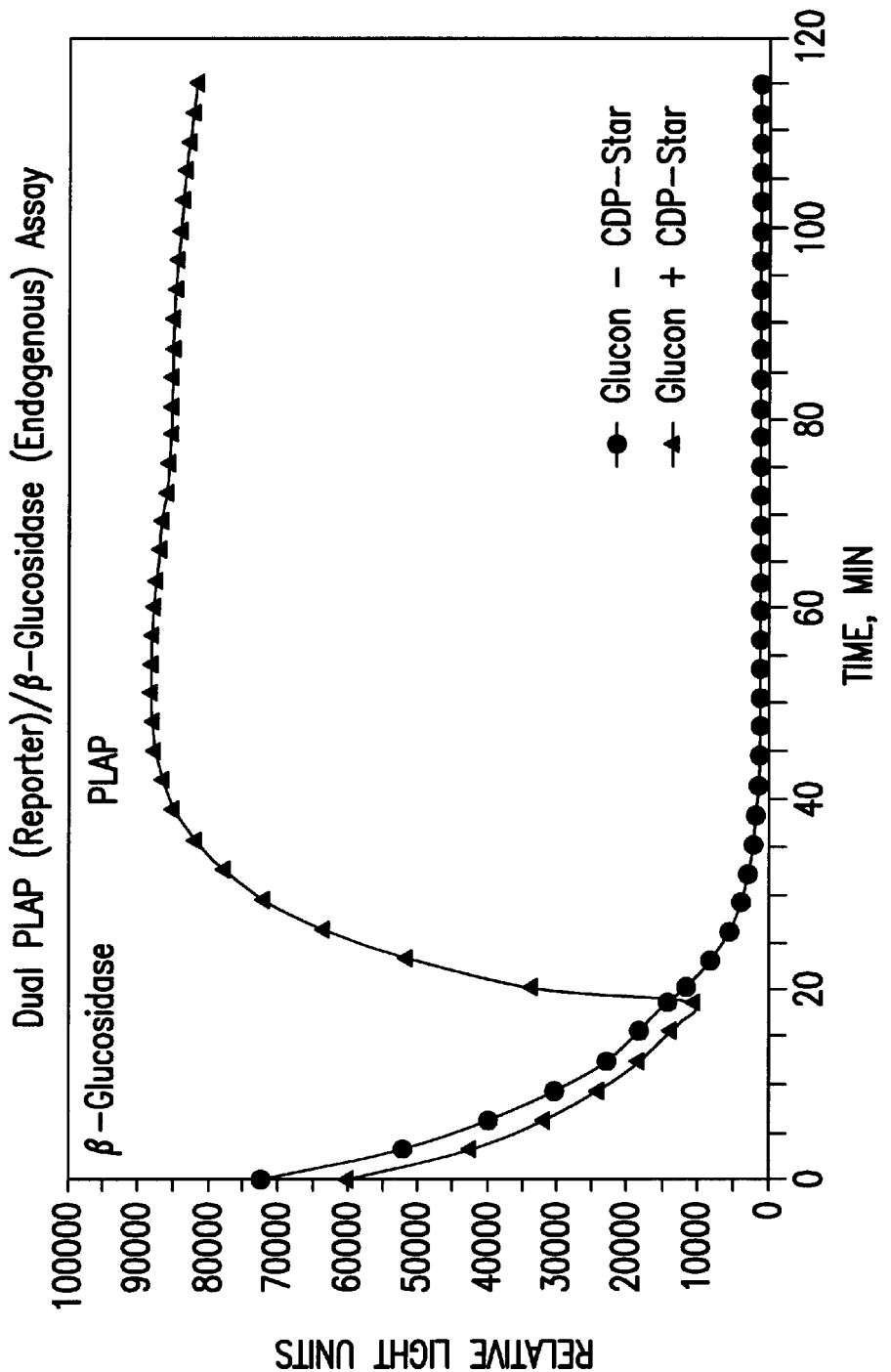
FIG. 6 provides graphical illustration of the kinetics of a dual enzyme assay for PLAP (reporter enzyme) and β-glucosidase (endogenous enzyme).

AP3T3b cells, a stably transfected BALB/3T3 derivative that constitutively expresses non-secreted placental alkaline phosphatase, were seeded into clear-bottom/white-side tissue culture-treated 96-well microplates in DMEM/10% CS ($1.2 \times 10^4$ cells/well). Prior to performing the assay, the culture medium was removed from the wells and the cells were washed once with 200 µl of PBS. All incubations were performed at room temperature. A β-glucosidase reaction buffer containing sodium phosphate, pH 5.5, MgSO$_4$, L-homoarginine, Triton X-100, and Glucon™ was added (50 µl/well) and the plates were incubated for 15 min. An accelerator solution (100 µL/well) containing Sapphire-II™ enhancer was then injected and light emission was measured immediately for 1 sec/well in a TR717 microplate luminometer. After approximately a 15 min delay, CDP-Star® was added (50 µl/well) and PLAP-catalyzed light emission was repeatedly measured (1 sec/well). The light signal from the endogenous β-glucosidase-catalyzed reaction was measured first. It is noted that in this reaction, the enzymatic deglycosylation of the 1,2-dioxetane substrate produces an anion intermediate that accumulates during the initial 15 min. incubation. The addition of the accelerator solution triggers light emission from the decomposition of the anion, and inactivates the β-glucosidase enzyme activity. The β-glucosidase-catalyzed light emission decayed within a few minutes. The light signal was almost completely decayed 40 min. following the addition of the accelerator, as seen in the reaction without CDP-Star®. Finally, CDP-Star® was added to initiate placental alkaline phosphatase-catalyzed light emission. Glow light emission kinetics were obtained with the maximum intensity at approximately 20 min. following substrate addition. The results of the assay are shown in FIG. 6.

Example 7

Detection Range of PLAP (Reporter)/β-Glucosidase (Endogenous) Assay

Figure 7:
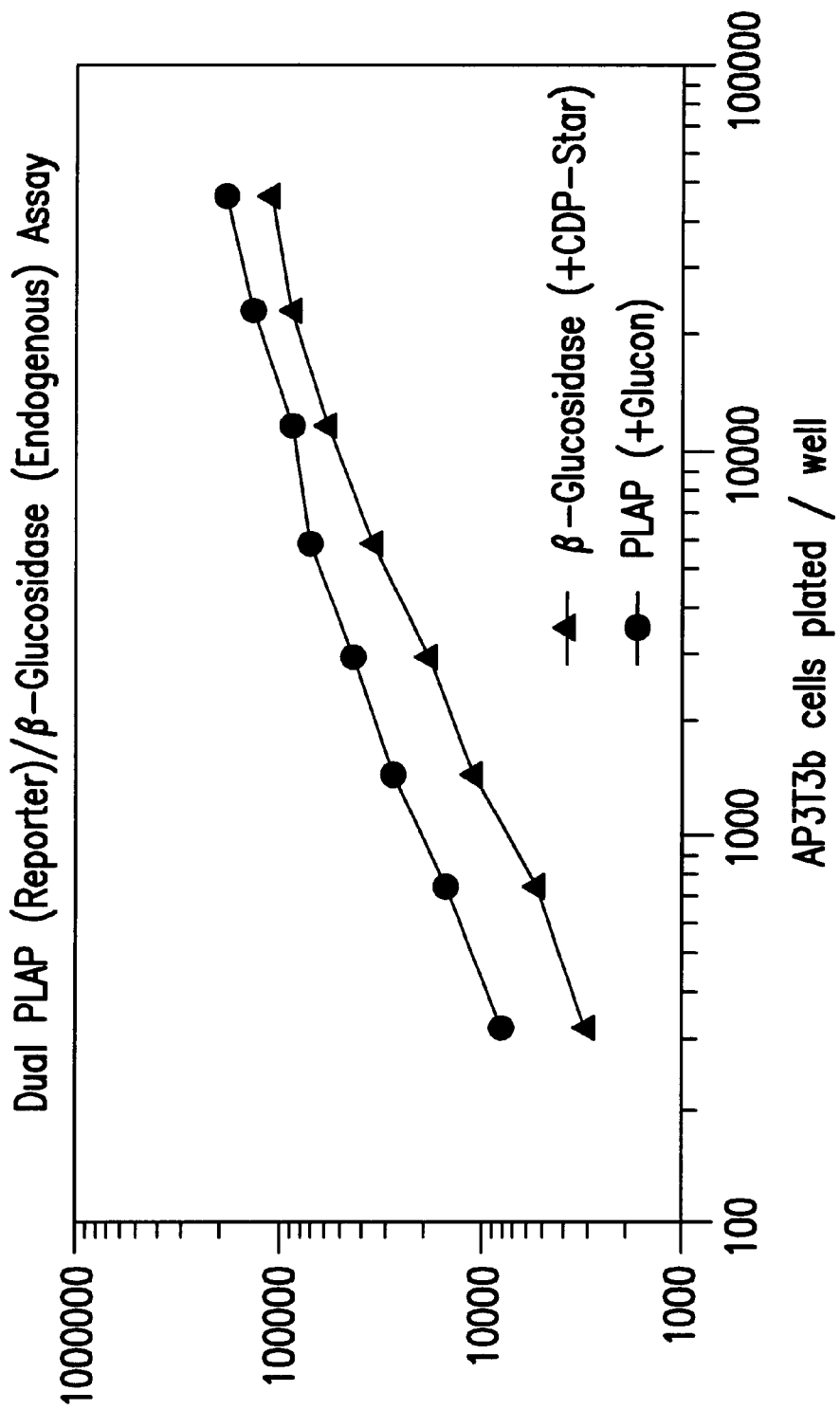
FIG. 7 provides graphical illustration of the detection range of a dual enzyme assay for PLAP (reporter enzyme) and β-glucosidase (endogenous enzyme).

AP3T3b cells, a stably transfected BALB/3T3 derivative that constitutively expresses non-secreted placental alkaline phosphatase, were seeded into clear-bottom/white-side tissue culture-treated 96-well microplates in DMEM/l0% CS. Prior to performing the assay, the culture medium was removed from the wells and the cells were washed once with 200 µl of PBS. All incubations were performed at room temperature. A β-glucosidase reaction buffer containing sodium phosphate, pH 5.5, MgSO$_4$, L-homoarginine, Triton X-100, and Glucon® substrate was added (50 µl/well) and the plates were incubated for 15 min. An accelerator solution (100 µl/well) containing Sapphire-II™ enhancer was then injected and light emission was measured immediately for 1 sec/well in a TR717 microplate luminometer. After approximately a 15 min. delay, a dilution of CDP-Star® substrate was added (50 μl/well), and PLAP-catalyzed light emission was measured (1 sec/well). Quantitation of both PLAP reporter enzyme and endogenous β-glucosidase activity was achieved with a linear range over two orders of magnitude, i.e., approximately 300–50,000 cells/well. The results of the assay are shown in FIG. 7. The detection sensitivity of each enzyme obtained with the dual protocol is identical to that obtained when each is measured alone (by including only a single substrate in the assay protocol). Thus, the sensitivity of PLAP detection is not affected by residual signal from Glucon™.

All references cited herein are incorporated in their entirety.

The invention has been described generically and in detail with particular references to the preferred embodiments thereof and with reference to specific examples. However, it will be appreciated that modifications and improvements within the spirit and scope of this invention may be made by those ordinarily skilled in the art upon considering the present disclosure. Unless excluded by the recitations of the claims set forth below, these variations remain within the scope of the invention.

What is claimed is:

1. An assay for measuring the activity of multiple enzymes in a single aliquot of a sample comprising:
   (a) quantifying the activity of an enzyme by measuring the light signal produced by the degradation of an enzyme substrate specific for said enzyme by said enzyme;
   (b) repeating step (a) for each enzyme present in said aliquot that is to be measured;
      wherein said enzymes are selected from the group consisting of reporter enzymes and endogenous enzymes;
      wherein at least one of said enzymes is an endogenous enzyme; and
      wherein the activity of a first enzyme is decreased prior to quantifying the activity of a second enzyme.

2. The assay of claim 1, wherein said first enzyme activity is decreased by altering the pH of said aliquot.

3. The assay of claim 1, wherein said first enzyme activity is decreased by heating said aliquot.

4. The assay of claim 1, wherein said first enzyme activity is decreased by inactivating said first enzyme by adding an inhibitor.

5. The assay of claim 1, wherein said first enzyme activity is decreased by allowing the reaction between said first enzyme and a first enzyme substrate to proceed until said first enzyme substrate is substantially degraded.

6. The assay of claim 1, wherein said first enzyme activity is decreased by decreasing the amount of a first enzyme substrate.

7. The assay of claim 1, wherein said first enzyme activity is decreased by adding an accelerator solution.

8. The assay of claim 1, wherein an enhancer is added to enhance said light signal.

9. The assay of claim 8, wherein said enhancer is selected from the group consisting of bovine serum albumin, human serum albumin and polymeric quaternary onium salts.

10. The assay of claim 9, wherein said polymeric quaternary onium salt is selected from the group consisting of polyvinylbenzyltrimethyl ammonium chloride, polyvinylbenzyl tributyl ammonium chloride, polyvinylbenzyl benzyldimethylammonium chloride, polyvinylbenzyltributyl phosphonium chloride, polyvinyl tributyl sulfonium chloride, poly(benzyldimethylvinylbenzyl)ammonium chloride, sodium fluorescein, poly(benzyltributyl) ammonium chloride, sodium fluorescein, quaternary ammonium-phosphonium polymers, ammonium-sulfonium polymers and sulfonium-phosphonium polymers.

11. The assay of claim 1, wherein an enzyme detection buffer comprising an endogenous enzyme substrate and an enhancer is added to said aliquot subsequent to the quantification of the reporter enzyme.

12. The assay of claim 1, wherein a first reporter enzyme, a second reporter enzyme, and an endogenous enzyme are the only enzymes to be measured, wherein a first reporter enzyme substrate and a second reporter enzyme substrate are present in said aliquot during the quantification of said first reporter enzyme; wherein the light produced by degradation of said first reporter enzyme substrate occurs at a pH at which the product of the degradation of said second reporter enzyme substrate does not produce light.

13. The assay of claim 1, wherein a first reporter enzyme, a second reporter enzyme, and an endogenous enzyme are the only enzymes to be measured, wherein a second reporter enzyme substrate is absent from said aliquot during the quantification of said first reporter enzyme and the activity of said second reporter enzyme is induced by the addition of a second reporter.

14. The method of claim 13, wherein an endogenous enzyme substrate is added subsequent to the quantification of said second reporter enzyme.

15. A kit for detecting the activity of multiple enzymes in a single aliquot of a sample comprising:
   reagents for quantifying each enzyme;
   substrates for each of said enzymes; and
   an accelerator solution containing a water soluble polymeric enhancer molecule;
   wherein at least one of said multiple enzymes is an endogenous enzyme.

16. The kit according to claim 15, wherein at least one of said substrates is a dioxetane.

17. The kit according to claim 16, wherein said dioxetane has the formula I

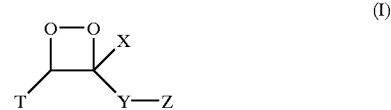

wherein T is a substituted or unsubstituted cycloalkyl ring having between 6 and 12 carbon atoms or a polycycloalkyl group bonded to the 4-membered dioxetane ring by a spiro linkage; Y is a fluorescent chromophore; X is hydrogen, a straight chain or branched chain alkyl or heteroalkyl group, an aryl group, a heteroaryl group, a heteroalkyl group, an aralkyl group, an alkaryl group, or an enzyme-cleavable group; Z is hydrogen, hydroxyl, or an enzyme-cleavable group;
   provided that at least one of X or Z must be an enzyme-cleavable group;
   wherein the enzyme-cleavable group is cleaved by an enzyme to thereby form a negatively charged group bonded to the dioxetane which decomposes to form a luminescing substance; and
   wherein said negatively charged group includes the group Y.

18. The kit according to claim 15, wherein said polymeric enhancer is selected from the group consisting of bovine serum albumin, human serum albumin and quaternary onium salts.

19. The kit according to claim 18, wherein said quaternary onium salts are selected from the group consisting of polyvinylbenzyltrimethyl-ammonium chloride, polyvinylbenzyltributylammonium chloride, polyvinylbenzyl benzyldimethylammonium chloride, polyvinylbenzyltributyl phosphonium chloride, poly(benzyldimethylvinylbenzyl) ammonium chloride, poly(benzyltributyl)ammonium chloride and sodium fluorescein.

20. The kit according to claim 15, wherein said polymeric enhancer has a pH of from about 8 to about 14.

21. The assay according to claim 1, wherein said sample is a preparation of a cell lysate.

22. The assay according to claim 1, wherein said sample comprises whole cells in culture media.

23. The assay according to claim 1, wherein said sample comprises whole cells without culture media.

24. The assay according to claim 23, wherein said sample is washed prior to assay.

25. The assay according to claim 23, wherein said sample is not washed prior to assay.

26. The assay according to claim 22, wherein said whole cells are washed prior to assay.

27. An assay for measuring the activity of multiple enzymes in a single aliquot of a sample comprising:
(a) quantifying the activity of an enzyme by measuring the light signal produced by the degradation of an enzyme substrate specific for said enzyme by said enzyme;
(b) repeating step (a) for each enzyme present in said aliquot that is to be measured;
wherein said enzymes are selected from the group consisting of reporter enzymes and endogenous enzymes;
wherein at least one of said enzymes is an endogenous enzyme; and
wherein the activity for each enzyme measured is quantified simultaneously.

28. The assay of claim 27, wherein the step of quantifying the activity of each enzyme measured is performed sequentially for each enzyme measured.

29. An assay for simultaneously measuring the activity of multiple enzymes in a single aliquot of a sample comprising:
simultaneously quantifying the activity of enzymes by simultaneously measuring light signals produced by the degradation of enzyme substrates specific for each of said enzymes by said enzymes;
wherein said enzymes are selected from the group consisting of reporter enzymes and endogenous enzymes;
wherein at least one of said enzymes is an endogenous enzyme;
wherein said light signals are distinguishable from each other; and
wherein one or more enhancers are added to enhance said light signals.

30. The assay according to claim 29, wherein said enhancer is selected from the group consisting of bovine serum albumin, human serum albumin and polymeric quaternary onium salts.

31. The assay according to claim 30, wherein said polymeric quaternary onium salt is selected from the group consisting of polyvinylbenzyltrimethyl ammonium chloride, polyvinylbenzyl tributyl ammonium chloride, polyvinylbenzyl benzyldimethylammonium chloride, polyvinylbenzyltributyl phosphonium chloride, polyvinyl tributyl sulfonium chloride, poly(benzyldimethylvinylbenzyl)ammonium chloride, sodium fluorescein, poly(benzyltributyl) ammonium chloride, sodium fluorescein, quaternary ammonium-phosphonium polymers, ammonium-sulfonium polymers and sulfonium-phosphonium polymers.

* * * * *